United States Patent [19]

Benazzi et al.

[11] Patent Number: 5,646,086

[45] Date of Patent: Jul. 8, 1997

[54] ALKYLATION CATALYST FOR $C_4$-$C_5$ ISOPARAFFINS USING AT LEAST ONE $C_2$-$C_6$ OLEFIN

[75] Inventors: Eric Benazzi, Montesson; Jean-François Joly, Paris; Christian Marcilly, Houilles, all of France

[73] Assignee: Institut Francais Du Petrole, Rueil-Malmaison, France

[21] Appl. No.: 433,961

[22] Filed: May 4, 1995

[30] Foreign Application Priority Data

May 4, 1994 [FR] France ................. 94 05493

[51] Int. Cl.⁶ ............ B01J 21/02; B01J 27/02; C07C 2/58
[52] U.S. Cl. .......... 502/202; 502/216; 585/724; 585/730; 585/731
[58] Field of Search ............... 502/202, 216; 585/724, 730, 731

[56] References Cited

U.S. PATENT DOCUMENTS

| | | |
|---|---|---|
| 2,355,339 | 8/1944 | Story .......................... 585/724 |
| 5,233,119 | 8/1993 | Kallenbach et al. .......... 585/721 |
| 5,292,986 | 3/1994 | Abbott ........................ 585/730 |
| 5,326,923 | 7/1994 | Cooper et al. ............... 585/724 |
| 5,420,093 | 5/1995 | Joly et al. ................... 585/731 |
| 5,475,184 | 12/1995 | Joly et al. .................. 502/202 |
| 5,489,564 | 2/1996 | Wu ............................. 502/202 |
| 5,489,728 | 2/1996 | Benazzi et al. ............. 502/202 |
| 5,489,730 | 2/1996 | Joly et al. ................... 502/202 |

FOREIGN PATENT DOCUMENTS

| | | | |
|---|---|---|---|
| 0 433 954 | 6/1991 | European Pat. Off. | .......... C07C 2/62 |
| 0 539 277 | 4/1993 | European Pat. Off. | ....... B01J 27/053 |
| 0 542 612 | 5/1993 | European Pat. Off. | ....... B01J 27/053 |

*Primary Examiner*—Glenn A. Caldarola
*Assistant Examiner*—Patricia L. Hailey
*Attorney, Agent, or Firm*—Millen, White, Zelano & Branigan, P.C.

[57] ABSTRACT

A catalyst comprising a porous organic or mineral support, preferably silica, and an acidic phase containing $B(OSO_2CF_3)_3$ and at least one acid selected from the group formed by sulphuric acid ($H_2SO_4$) and trifluoromethane sulphonic acid ($CF_3SO_3H$), said support having been impregnated with said acidic phase and said support prior to impregnation having a total pore volume of 0.1–0.6 cm³/g, said catalyst being essentially constituted by particles with an average diameter of between 0.1 and 30 μm, said catalyst being characterized in that said acidic phase contains:

between 0.1 and 70% by weight of $B(OSO_2CF_3)_3$;

between 0 and 90% by weight of $H_2SO_4$;

between 0 and 90% by weight of $CF_3SO_3H$.

is suitable for the catalytic alkylation of isobutane and/or isopentane in the presence of at least one olefin containing 2 to 6 carbon atoms per molecule, preferably 3 to 6 carbon atoms per molecule.

21 Claims, No Drawings

ALKYLATION CATALYST FOR $C_4$-$C_5$ ISOPARAFFINS USING AT LEAST ONE $C_2$-$C_6$ OLEFIN

The present invention concerns a catalyst comprising a porous organic or mineral support, preferably silica, and an acidic phase containing $B(OSO_2CF_3)_3$ and at least one acid selected from the group formed by sulphuric acid ($H_2SO_4$) and trifluoromethane sulphonic acid ($CF_3SO_3H$), said support having been impregnated with said acidic phase. The invention also concerns the preparation and use of the catalyst for the catalytic alkylation of an isoparaffin (isobutane and/or isopentane) in the presence of at least one olefin containing 2 to 6 carbon atoms per molecule.

It is particularly important for spark ignition internal combustion engines, in particular those with high compression ratios, to use fuels with high octane numbers, i.e., essentially constituted by highly branched paraffin hydrocarbons. Alkylation of isoparaffins (isobutane and/or isopentane) by olefins containing 3 to 6 carbon atoms per molecule can produce such products. This reaction requires the use of highly acidic catalysts, primarily to reduce side reactions such as hydride abstraction from the olefin and polymerisation, which produces less branched hydrocarbons with low octane numbers and unsaturated hydrocarbons, also cracking reactions and dismutation reactions.

Existing processes for the production of hydrocarbons by alkylation of isobutane with olefins generally use either sulphuric acid or hydrofluoric acid as a catalyst. In these processes, the acidic catalyst constitutes a liquid phase which is brought into contact with the liquid isobutane-olefin mixture to form an emulsion. These processes are costly and pose substantial problems as regards personnel and environmental safety. In order to overcome these problems, catalytic systems other than those using liquid phase sulphuric acid and hydrofluoric acid have been sought.

To catalyse the alkylation of isoparaffins by olefins, acidic catalysts have been proposed which use a number of acidic solids of different natures, such as molecular sieves, macroreticular resins which may be combined with $BF_3$, Lewis acids and/or Brönsted acids deposited on a variety of inorganic supports, chlorinated aluminas, graphites with intercalated Lewis and/or Brönsted acids, and anions deposited on oxide supports such as $ZrO_2/SO_4$. These solids produce branched isoparaffins but suffer from a number of major defects, among them the use of isobutane/olefin molar ratios which are often very high to limit secondary reactions, and low stability of catalytic activity with time (inhibition of the catalyst by deposition of unsaturated oligomers), requiring frequent regeneration. Further, the low acidity of certain acidic solids, such as molecular sieves, requires the use of high reaction temperatures which inhibit the production of hydrocarbons with high octane numbers.

European patent application EP-A-0 539 277 describes a catalyst containing silica and a solid acidic phase comprising sulphuric acid, the silica of that application having a pore volume of between 0.005 and 1.5 $cm^3/g$, and a specific surface area of between 0.01 and 1500 $m^2/g$. The acidic phase optionally includes an additive selected from the group formed by $H_3PO_4$, $B(OH)_3$, $BF_4H$, $FSO_3H$, $CF_3CO_2H$, $SbF_5$, $CF_3SO_3H$ and $SO_3$.

French patent application, national registration number 93/04735, describes a catalyst comprising an organic or mineral porous support and a mixture constituted by sulphuric acid, trifluoromethane sulphonic acid and, optionally, water.

The present invention concerns a catalyst comprising a porous organic or mineral support, preferably silica, and an acidic phase comprising $B(OSO_2CF_3)_3$ and at least one acid from the group formed by sulphuric acid ($H_2SO_4$) and trifluoromethane sulphonic acid ($CF_3SO_3H$), said support being impregnated with said acidic phase, said catalyst being essentially constituted by particles with an average diameter of between 0.1 and 30 μm (1 μm=$10^{-6}$M), preferably between 5 and 30 μm, said catalyst being characterised in that said acidic phase comprises:

- between 0.1 and 70% by weight, preferably between 0.2 and 65% by weight, of $B(OSO_2CF_3)_3$;
- between 0 and 90% by weight, preferably between 0 and 80% by weight, of $H_2SO_4$;
- between 0 and 90% by weight, preferably between 0 and 85% by weight, of $CF_3SO_3$.

The invention also concerns the preparation and use of said catalyst for the catalytic alkylation of at least one isoparaffin selected from the group formed by isobutane and isopentane (i.e., isobutane and/or isopentane: isobutane, or isopentane, or isobutane and isopentane) in the presence of at least one olefin containing 2 to 6 carbon atoms per molecule, preferably 3 to 6 carbon atoms per molecule.

The catalyst of the present invention surprisingly produces improved catalytic performances compared with those described in European patent application EP-A-0 539 277 and in French patent application 93/04735.

The concentration of sulphuric acid is advantageously between 90% and 100% by weight, preferably between 97% and 100% by weight, more preferably between 98% and 100% by weight.

The concentration of trifluoromethane sulphonic acid is advantageously between 95% and 100% by weight, preferably between 98% and 100% by weight.

The $B(OSO_2CF_3)_3$ in the acidic phase of the catalyst of the invention is prepared using methods which are known to the skilled person. By way of non limiting example, preferred methods which can be mentioned are firstly, reacting a boron trihalide $BX_3$ (where X is a halogen, preferably Cl or Br) with 3 molar equivalents of trifluoromethane sulphonic acid ($CF_3SO_3H$) in the reaction:

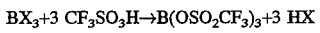

The second preferred method of the invention consists in reacting one mole of boron trihalide $BX_3$ (where X is a halogen, preferably Cl or Br) with 3 molar equivalents of silver trifluoromethane sulphonate $CF_3SO_3Ag$:

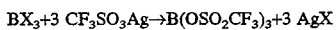

The two above reactions, exemplifying the first and second preferred methods of the invention, are described in particular by Engelbrecht et al, in Z Anorg Chem, 1977, 433, 19, and by G. A. Olah et al, in J Org Chem, 1984, 49, 4591–4594.

When using silica as the support, it can contain impurities such as oxides, alkalis, alkaline-earths, aluminium compounds or any other impurity known to the skilled person, the total quantity of these impurities generally not exceeding 2% by weight with respect to the silica.

The organic or mineral porous support, preferably silica, is generally such that, before impregnation by the acidic phase, the specific surface area is between 0.1 and 1500 $m^2/g$, and its total pore volume is between 0.1 and 0.6 $cm^3/g$, preferably between 0.1 and 0.4 $cm^3/g$. In addition, it is generally essentially constituted by particles with an average diameter of between 0.1 and 30 μm, preferably between 5 and 30 μm.

The acidic phase generally occupies between 80% and 100% of the total pore volume of the support, preferably between 90% and 100% of the pore volume.

The weight content of the acidic phase in the catalyst is generally between 1% and 40% by weight, preferably between 1% and 30% by weight.

The preparation process for the catalyst of the invention comprises two steps. In the first step, the porous organic or mineral support is calcined at a temperature of more than 50° C., preferably more than 80° C., more preferably between 150° C. and 600° C., for example at about 500° C. This calcining step usually lasts between 10 minutes and 50 hours, preferably between 15 minutes and 25 hours. Calcining is generally carried out in the presence of dry air or a dry air/nitrogen mixture at a flow rate of between 0.001 and 10 l/h/g, preferably between 0.1 and 5 l/h/g. The second step consists of impregnating the calcined support with the acidic phase. This step can be effected using any technique known to the skilled person. An acidic phase preparation step can be added to this preparation method, prior to the impregnation step.

The catalyst of the present invention is used in a process in which the alkylation reaction of isobutane by olefins is carried out under improved conditions. In particular, since the reaction is characterised by high exothermicity (about 83.6 kJ/mole of butene transformed if the olefin is butene and if the isoparaffin is isobutane), the use of the catalyst of the invention produces good temperature homogeneity and reactant concentration.

The operating conditions, in particular the temperature and pressure in the isobutane alkylation process using the catalyst of the present invention, are generally selected so that the mixture, constituted by the isoparaffin, olefin(s) and reaction products, is liquid. In addition, it is important that the catalyst is immersed in the liquid to ensure good liquid-solid contact.

The catalyst of the invention is advantageously used in the isobutane and/or isopentane alkylation reaction zone with at least one olefin containing 2 to 6 carbon atoms per molecule, preferably 3 to 6 carbon atoms per molecule, in the liquid phase and mixed with the isoparaffin and/or isoparaffin mixture. The catalyst of the invention can be used in an expanded bed, in an almost ideally agitated reaction zone or in a circulating bed, preferably in a process using a continuous liquid phase, the catalyst being used in the form of a suspension in the two operative embodiments described below.

In a first preferred operating embodiment for the catalyst of the invention, a reaction zone using almost perfect mixing is used, i.e., a perfect mix or a near perfect mix (agitated or Grignard vessel), using at least one agitation means, for example at least one propeller, to obtain sufficient agitation of the catalyst in suspension in the liquid hydrocarbon phase, this phase generally including the isoparaffin (isobutane and/or isopentane), at least one olefin, optionally at least one inert diluent (for example propane and n-butane) and the alkylation reaction products. The feed to be converted, constituted by isobutane and/or isopentane and at least one olefin, can for example be introduced in the liquid form at at least one point into the liquid hydrocarbon phase present in the reaction zone.

In a second preferred operating embodiment, the catalyst of the invention in suspension in the hydrocarbon phase is a mobile bed in co-current mode, i.e., a circulating bed. In this embodiment, the catalyst in suspension in the hydrocarbon liquid phase generally including the isoparaffin (isobutane and/or isopentane), at least one olefin, optionally at least one inert diluent (for example propane or n-butane) and the alkylation reaction products, circulates from bottom to top in the reaction zone. The assembly constituted by the catalyst suspension in the hydrocarbon phase then circulates through at least one heat exchanger and at least one pump before being reintroduced to the inlet to the reaction zone. The feed to be converted, constituted by isobutane and/or isopentane and at least one olefin, is introduced either in the liquid form, or in the gaseous state at at least one point of the reaction zone.

In the two types of embodiment described above, the isoparaffin (isobutane and/or isopentane) which is either unconverted or has been introduced in excess with respect to the stoichiometry of the reaction, is generally recycled after separation of the alkylate, either by direct introduction into the reaction zone, or by mixing with the feed to be converted.

The isoparaffin-olefin mixture is generally introduced into the reaction zone at an hourly space velocity, expressed as the weight of olefin introduced per unit weight of catalyst per hour (pph), of between 0.001 and 10 $h^{-1}$, preferably between 0.002 and 2 $h^{-1}$. Mixing can also be effected within the reaction zone. In all cases, the mixture thus constituted is in the reaction zone under temperature and pressure conditions in which the hydrocarbon mixture remains liquid on the catalyst.

The reaction temperature is generally less than −10° C., preferably 0° C. and more preferably less than −3° C. The pressure in the reaction zone is generally sufficient to maintain the hydrocarbons in the liquid state in this zone.

In order to limit secondary reactions, an excess of isoparaffin over olefin can be used. By way of example, in the case of alkylation of isobutane by a butene, the isobutane can be introduced pure into the feed or in the form of a mixture of butanes containing, for example, at least 40% of isobutane. A pure butene or a mixture of butene isomers can also be introduced. In all cases, the molar ratio of isobutane/butene(s) in the feed is generally between 1 and 100, preferably between 3 and 50 and more preferably between 5 and 15.

The reaction products can be regularly monitored by measurement of the bromine index, for example using the method described in French Standard Pr.M 07.071, March 1969.

When the catalyst and the reaction conditions are carefully selected (in particular the temperature), the catalyst of the invention produces products of the alkylation of at least one isoparaffin by at least one olefin which are of importance as engine fuels and petrol constituents and which contain, for example, at least 60 mole % of paraffins containing 8 carbon atoms per molecule and less than 1 mole % of unsaturated compounds, the paraffins containing 8 carbon atoms per molecule containing 70 to 98 mole % of trimethylpentanes.

A further advantage of the catalyst of the present invention is the possibility of alkylating isobutane at low temperature, with mixtures of olefins containing 3 to 6 carbon atoms per molecule, where the proportion of olefins containing more than 4 carbon atoms per molecule is very high.

The following examples illustrate the invention without in any way limiting its scope.

EXAMPLE 1

Preparation of catalyst 1, in accordance with the invention 30 g of silica with a total pore volume of 0.21 $cm^3/g$, a specific surface area of 265 $m^2/g$ and an average particle diameter of 11 μm was activated by drying at 150° C. for 12 hours. The activated silica was stored under nitrogen. 20 g of the dehydrated silica was then dry impregnated with 7.1 g of a mixture constituted by:

5.1 g of a $H_2SO_4$ solution (100 weight %)

2.0 g of $B(OSO_2CF_3)_3$.

The composition by weight of the acidic phase was as follows:

$H_2SO_4$: 71.8%

$B(OSO_2CF_3)_3$: 28.2%

The solid obtained, catalyst 1, had an acidic phase concentration of 26.2 weight %. It was stored under argon at −18° C.

Alkylation of isobutane by but-1-ene with catalyst 3

20 g of catalyst 1, prepared as above, was introduced into a glass Fischer & Porter reactor with a volume of 360 ml which had been purged with argon. The reactor containing the catalyst was then sealed, placed under low vacuum, then cooled to a temperature of −20° C.

157 cm$^3$ of isobutane was then added to the reactor containing the catalyst, with stirring (propeller), the reactor being immersed in a cold bath at −20° C. The catalyst 1+isobutane system was stirred for 30 minutes to homogenise the temperature.

6 g per hour of but-1-ene was added steadily, over a total period of 6 hours, the temperature of the reactor being held at −7° C. for the whole of the injection period.

After reaction, the hydrocarbon phase was extracted from the reactor, then the isobutane was slowly evaporated and the alkylate was recovered and analysed by vapour phase chromatography. The composition by weight is given in Table 1. 100% of the olefin was converted.

EXAMPLE 2

Preparation of catalyst 2, not in accordance with the invention

Catalyst 2 was prepared using 20 g of the same silica as that used to prepare catalyst 1, under identical calcining conditions. The activated solid was stored under argon. 20 g of the calcined silica was then dry impregnated with 7.1 g of sulphuric acid (100 weight %). The solid obtained, catalyst 2, had an acid phase concentration of 26.2 weight %. It was stored protected from moisture and under argon at −18° C.

Alkylation of isobutane by but-1-ene with catalyst 2

The catalytic test for the alkylation of isobutane using but-1-ene was repeated using the same experimental conditions as those described for Example 1. the results are shown in Table 1.

TABLE 1

| Alkylate composition (weight %) | Example 1, catalyst 1 in accordance with invention | Example 2, catalyst 2 not in accordance with invention |
|---|---|---|
| % C$_5$–C$_7$ | 3.5 | 11.9 |
| % C$_8$ | 89.8 | 71.2 |
| % C$_9$$^+$ | 6.7 | 16.9 |

We claim:

1. A catalyst comprising a porous organic or mineral support and an acidic phase comprising $B(OSO_2CF_3)_3$ and at least one acid selected from the group consisting of sulphuric acid ($H_2SO_4$) and trifluoromethane sulphonic acid ($CF_3SO_3H$), said support being impregnated with said acidic phase and said support prior to impregnation having a total pore volume between 0.1 and 0.6 cm$^3$/g, said catalyst being essentially constituted by particles with an average diameter of between 0.1 and 30 μm, said catalyst being characterised in that said acidic phase comprises:

between 0.1 and 70% by weight of $B(OSO_2CF_3)_3$;

between 0 and 90% by weight of $H_2SO_4$;

between 0 and 90% by weight of $CF_3SO_3H$; with the provision that the combined total of $H_2SO_4$ and $CF_3CO_3H$ is above zero.

2. A catalyst according to claim 1, essentially constituted by particles with an average diameter of between 5 and 30 μm.

3. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 2.

4. A catalyst according to claim 1, in which the concentration of the acidic phase in the catalyst is between 1% and 40% by weight.

5. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 4.

6. A catalyst according to claim 1, in which said support is silica.

7. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 6.

8. A process for preparing a catalyst according to claim 1, comprising at least two steps, in which in the first step the support is calcined at a temperature of more than 50° C. for a period of between 10 minutes and 50 hours, and in the second step said calcined support is impregnated with said acidic phase.

9. A process according to claim 8, in which the $B(OSO_2CF_3)_3$ is obtained using one of methods (a) or (b) as follows:

a) reacting a boron trihalide $BX_3$, wherein, with 3 molar equivalents of trifluoromethane sulphonic acid ($CF_3SO_3H$) in accordance with the reaction:

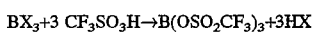

b) reacting one mole of boron trihalide $BX_3$, wherein, with 3 molar equivalents of silver trifluoromethane sulphonate $CF_3SO_3Ag$:

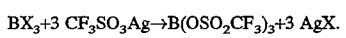

10. The process according to claim 9, in which the reaction temperature is less than +10° C. and the pressure in the reaction zone is sufficient to maintain the hydrocarbons in the liquid state in said zone.

11. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 1.

12. The process according to claim 11, in which the catalyst in the reaction zone is an almost perfect mixture.

13. The process according to claim 11, wherein the catalyst is in the form of a mobile bed and reactants and the bed run cocurrently.

14. A catalyst according to claim 1, wherein the total pore volume of the porous support prior to impregnation is 0.1–0.4 cm$^3$/g.

15. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 14.

16. A catalyst according to claim 1, wherein the porous support has a specific surface area between 0.1 and 1,500 m²/g.

17. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 16.

18. A catalyst according to claim 1, in which the concentration of the acidic phase in the catalyst is between 1% and 30% by weight.

19. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 18.

20. A catalyst according to claim 1 prepared by a process, in which in the first step the support is calcined at a temperature of between 150° C. and 600° C. for a period of between 10 minutes and 50 hours, and in the second step said calcined support is impregnated with said acidic phase.

21. In a process comprising catalytically alkylating isobutane, isopentane, or a mixture thereof in a reaction zone in the presence of at least one olefin containing 2 to 6 carbon atoms per molecule the improvement wherein the catalyst is the catalyst of claim 20.

* * * * *